United States Patent [19]

Schädeli

[11] Patent Number: 5,210,003

[45] Date of Patent: May 11, 1993

[54] ACID LABILE DISSOLUTION INHIBITORS AND POSITIVE- AND NEGATIVE-ACTING PHOTOSENSITIVE COMPOSITION BASED THEREON

[75] Inventor: Ulrich Schädeli, Granges-Paccot, Switzerland

[73] Assignee: Ciba-Geigy Corporation, Ardsley, N.Y.

[21] Appl. No.: 756,631

[22] Filed: Sep. 9, 1991

[30] Foreign Application Priority Data

Sep. 13, 1990 [CH] Switzerland ............ 2971/90

[51] Int. Cl.$^5$ ............................. G03C 1/492
[52] U.S. Cl. .................. 430/270; 430/176; 430/192; 430/325; 430/326; 430/905
[58] Field of Search ............. 430/270, 905, 176, 192, 430/325, 326

[56] References Cited

U.S. PATENT DOCUMENTS

| | | | |
|---|---|---|---|
| 3,779,778 | 12/1973 | Smith et al. | 96/115 |
| 4,514,168 | 4/1950 | Smith et al. | 260/333 |
| 4,517,227 | 5/1985 | Cassat | 430/167 |
| 4,908,381 | 3/1990 | Greenwald et al. | 514/460 |
| 5,110,633 | 5/1992 | Cassat et al. | 427/430.1 |
| 5,151,341 | 9/1992 | Kim | 430/270 |

FOREIGN PATENT DOCUMENTS

0424124 4/1991 European Pat. Off. ............ 430/270

OTHER PUBLICATIONS

SPIE, vol. 920, pp. 60–66 (1988), D. R. McLean et al. "Novalac Varied Deep-UV Resists".
J. American Chem. Soc. 70, pp. 4187–4189 (1948); W. F. Parham et al "The Protection of Hydroxyl Groups". Beilstein, Supplemental III, IV, vol. 17, pp. 1182–1195.
Polym. Mat. Sci. Eng. 61(1989), pp. 417–421, N. Hayashi et al. "Tetradropyranyl & Tetrahydrofuranol Protected Hydroxy Stryenes in Chemical Modification Resist Systems for KrF Excimer Laser Lithography".
Chem. Abstr., V. G. Kozyrev et al. vol. 13, No. 19, Nov. 9, 1970, pp. 356–357, 98,735Y.

*Primary Examiner*—Marion E. McCamish
*Assistant Examiner*—Janis L. Dote
*Attorney, Agent, or Firm*—JoAnn Villamizar; William A. Teoli, Jr.

[57] ABSTRACT

Non-polymeric compounds which contain at least one aromatic ring system carrying one or more one or more tetrahydropyranyloxy substituents of formula I

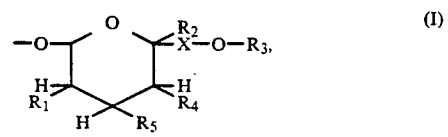

wherein
$R_1$ is hydrogen, halogen, alkyl, cycloalkyl, aryl, alkoxy or aryloxy,
$R_2$ is hydrogen, alkyl, cycloalkyl or aryl,
$R_3$ is a saturated or unsaturated hydrocarbon radical,
$R_4$ and $R_5$ are each independently of the other hydrogen, halogen, alkyl, alkoxy or aryloxy, and
X is a direct single bond or a methylene or ethylene bridge.

These compounds are especially suitable for the preparation of photoresist compositions which can be used both for the production of positive as well as negative images. The photoresists are preferably used for deep-UV microlithography.

7 Claims, No Drawings

ACID LABILE DISSOLUTION INHIBITORS AND POSITIVE- AND NEGATIVE-ACTING PHOTOSENSITIVE COMPOSITION BASED THEREON

The present invention relates to novel non-polymeric compounds containing at least one aromatic ring system carrying one or more special tetrahydropyranyloxy substituents, to compositions which contain said compounds, to processes for producing positive and negative images with the aid of said compositions and to the products obtainable by means of said processes.

Photoresist systems have long been known and are used typically for making printing plates, silverless photographic films, wiring boards and integrated circuits.

A special type of such photoresists consists of a compound A which, upon exposure to radiation, reacts to form a protic or Lewis acid, and at least one further compound B which is insoluble or virtually insoluble in any chosen solvent and prevents or substantially reduces the tendency of other compounds which may be present in the photoresist to dissolve in this solvent (dissolution inhibitor). Compound B reacts with the acid generated upon the exposure of compound A to radiation. In this reaction, compound B undergoes chemical change such that it becomes soluble in the chosen solvent and, as a consequence, the resist system can be dissolved at the irradiated areas in the chosen solvent.

As the acid generated upon exposure to radiation catalyses the reaction of compound B, only minor amounts of acid are necessary to be able to convert compound B by heating completely into the soluble form (chemical amplification).

Positive-working photoresist systems which are based on the principle outlined above are disclosed, inter alia, in U.S. Pat. No. 3,779,778. The dissolution inhibitors mentioned therein also include aryl compounds which contain tetrahydropyranyloxy groups which may in turn be alkyl- or phenyl-substituted. These photoresist systems are suitable for irradiation in the wavelength range from 300 to 700 nm. The acid formed by exposure to radiation catalyses the reaction of the dissolution inhibitor to remove the tetrahydropyran groups, resulting in the formation of the hydroxyaryl compounds which, in contrast to the unreacted dissolution inhibitor, are relatively readily soluble in aqueous alkaline solutions, so that the resist layer can be dissolved with such solutions at the exposed areas.

However, for preparing large-scale integrated circuits in particular, it is necessary to carry out exposure with radiation of shorter wavelength than that mentioned in the above U.S. patent specification for the photoresist systems disclosed therein. Exposure is often made in the deep-UV range (wavelength of c. 200–300 nm) in order that sufficiently fine structures can be imaged (deep-UV microlithography). The photoresist layers need to be much more sensitive than when radiating with wavelengths above 300 nm. The mercury vapour-pressure lamps often used for deep-UV microlithography have only a very minor amount of radiation at a wavelength of 254 nm, based on the amount of radiation of longer wavelength (365 nm and 436 nm). Photoresist systems containing a photosensitive acid generator and a dissolution inhibitor have also already been proposed for deep-UV microlithography (Dennis R. McKean, Scott A. MacDonald, Nicholas J. Clecak and C. Grant Wilson, "Novolak based deep-UV resists", SPIE, Vol. 920 Advances in Resist Technology and Processing V, p. 60–66 (1988)). The dissolution inhibitor used is a tert-butylcarbonate derivative of bisphenol A which, together with triphenylsulfonium hexafluoroantimonate and a novolak resin, forms a positive photoresist which is able to resolve structures of 1 μm.

It has now been found that novel compounds which contain specifically substituted tetrahydropyranyloxy groups attached to aromatic nuclei are particularly suitable dissolution inhibitors both for positive as well as negative photoresists, especially when high demands are made of the resolution of superfine structures.

Specifically, the invention relates to non-polymeric compounds containing at least one aromatic ring system which carries one or more tetrahydropyranyloxy substituents of formula I

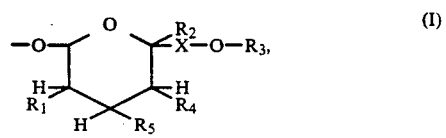

wherein
- R₁ is hydrogen, halogen, alkyl, cycloalkyl, aryl, alkoxy or aryloxy,
- R₂ is hydrogen, alkyl, cycloalkyl or aryl,
- R₃ is a saturated or unsaturated hydrocarbon radical,
- R₄ and R₅ are each independently of the other hydrogen, halogen, alkyl, alkoxy or aryloxy, and
- X is a direct single bond or a methylene or ethylene bridge.

Alkyl radicals R₁ and/or R₂ in formula I may be in chain conformation, i.e. straight-chain or branched alkyl radicals. Especially if—as is useful for photoresist utilities—it is desired that the melting points of the compounds of the invention shall not be too low, the chains of the alkyl radicals should not be too long. Very suitable in this case are alkyl radicals of 1 to 5 carbon atoms. Radicals having short chains also promote the solubility of the compounds in more polar solvents—also an advantage in certain cases. Typical examples of such alkyl radicals include methyl, ethyl, n-propyl, isopropyl, n-butyl, sec.-butyl, tert-butyl, n-pentyl, isoamyl. The most preferred alkyl radical for R₁ and/or R₂ is methyl.

Cycloalkyl radicals R₁ and/or R₂ are suitably those containing 1 to 8 carbon atoms, such as cyclopentyl, methyl-substituted cyclopentyl, cyclohexyl or cycloheptyl.

R₁ and/or R₂ as aryl is preferably phenyl or substituted phenyl. Suitable substituents of phenyl include alkyl and alkoxy, preferably each of 1 to 4 carbon atoms, or halogen. Larger aromatic system, for example naphthyl and still larger ones, cause the compounds of the invention to have a relatively strong individual absorption in the UV and/or visible range. These compounds are less suitable in particular for use as dissolution inhibitors for photoresists which are sensitive in the deep-UV range. One field of use for such compounds, however, would be as additives for X-ray-sensitive photoresists.

An alkoxy radical R₁ is preferably an alkoxy radical of 1 to 5 carbon atoms, typically methoxy, ethoxy, n-propoxy, isopropoxy or one of the different butoxy or pentoxy radicals.

$R_1$ as aryloxy is preferably phenoxy or substituted phenoxy and, if the individual absorption of the compounds of the invention is not a negative factor, is also a corresponding radical of larger aromatic systems such as naphthoxy. Suitable substituents of naphthoxy include alkyl or alkoxy, preferably each of 1 to 4 carbon atoms, and halogen. A halogen substituent $R_1$ is suitably fluoro, but preferably chloro and bromo and also iodo.

$R_3$ may be a straight-chain or branched or also a cyclic hydrocarbon radical. It may contain typically 1 to 20 carbon atoms. Particularly preferred radicals are short chain acyclic radicals of 1 to 8 carbon atoms, typically methyl, ethyl, n-propyl, isopropyl, n-butyl, sec.-butyl, tert-butyl, isobutyl, n-pentyl, isopentyl, isoamyl, n-hexyl, n-octyl or isooctyl, or the corresponding mono- or polyunsaturated alkenyl or alkynyl radicals, such as vinyl, ethynyl, 1-propenyl, allyl, 1-methylvinyl, butenyl, butadienyl, butynyl, pentenyl, pentadienyl, heptadienyl and the like, and aryl. Illustrative examples of aryl radicals are phenyl, substituted phenyl and naphthyl. Particularly suitable substituents of phenyl are again alkyl and alkoxy, each of 1 to 4 carbon atoms, or halogen. Exemplary of suitable non-aromatic cyclic hydrocarbon radicals $R_3$ are cyclopentyl, cyclopentenyl, cyclohexyl, cyclohexenyl or cyclohexadienyl. Most preferred, however, are alkyl chains of 1 to 5 carbon atoms, preferably methyl, ethyl and isobutyl, as well as phenyl. In addition to these radicals, particularly suitable radicals $R_3$ for the use as dissolution inhibitor in positive photoresists are often those which are able to form particularly stable carbonium ions, for example the allyl radical or other radicals $R_3$ having allylic unsaturation, as in the case of such radicals it is also relatively easy to cleave the ether linkage in $R_3$ with acid, so that the pyranyl group split off from the dissolution inhibitor by the irradiation can be readily further broken down into smaller constituents, whereby the solubility of the irradiated areas of the resist layer in customary developers is further enhanced.

$R_4$ and/or $R_5$ as alkyl or alkoxy radicals also preferably contain 1 to 5 carbon atoms. Such radicals are exemplified above in the definitions given for $R_1$ and $R_2$. $R_4$ and $R_5$ as aryloxy are preferably phenoxy or substituted phenoxy. Suitable substituents of phenoxy include alkyl and alkoxy, each preferably of 1 to 4 carbon atoms, or halogen. $R_4$ and $R_5$ as halogen have the same meanings as given previously for $R_1$ as halogen. Most preferably $R_4$ and $R_5$ are methyl or hydrogen.

Preferred compounds of this invention are those wherein $R_1$ in formula I is hydrogen, halogen, $C_1$–$C_5$alkyl, phenyl, substituted phenyl, $C_1$–$C_5$alkoxy, phenoxy or substituted phenoxy, $R_2$ is hydrogen, $C_1$–$C_5$alkyl or phenyl, $R_3$ is a saturated or unsaturated hydrocarbon radical of 1 to 20 carbon atoms and $R_4$ and $R_5$ are each independently of the other hydrogen, halogen, $C_1$–$C_5$alkyl, $C_1$–$C_5$alkoxy, phenoxy or substituted phenoxy.

The most preferred compounds, finally, are those in which $R_1$ is hydrogen, methyl or phenyl, $R_2$, $R_4$, $R_5$ are each hydrogen and $R_3$ is a saturated or unsaturated acyclic hydrocarbon radical of 1 to 8 carbon atoms or is phenyl, especially when $R_1$ is also hydrogen.

Preferred types of compounds are also those in which X is a direct bond, as they are particularly easy to obtain and also the acid cleavage of the ether linkage between the tetrahydropyran ring and the radical $R_3$ also proceeds with particular ease in this case.

The compounds of this invention are non-polymeric compounds. The term "non-polymeric", however, is not intended to exclude oligomers of a degree of polymerisation below about 10. The compounds normally contain a maximum of about 100, preferably a maximum of about 50, atoms in the molecule, this number including all carbon and hetero atoms but not the hydrogen atoms and any atom of the tetrahydropyranyloxy groups. Hetero atoms are preferably N, O, S, halogens, preferably F, Cl and Br, as well as Si. At least 75% of the atoms in the molecule of the compounds of the invention should belong to aromatic systems. The compounds of the invention conveniently contain at least two tetrahydropyranyloxy substituents of formula I and, furthermore, the total number of substituents of formula I present in the compounds should be at least so great that there is at least one substituent of formula I for every two aromatic rings in the compounds, in which connection the expression "aromatic rings" will be understood as meaning the individual aromatic rings of an aromatic system.

For photoresist utilities, the compounds of this invention conveniently contain, however, more than two tetrahydropyranyloxy substituents. In this case, not only a single tetrahydropyranyloxy group of formula I can be attached to an aromatic ring, but also two, three or possibly even more. The upper limit will, however, usually be kept by the steric conditions in the molecule to two or three groups of formula I per aromatic ring.

The aromatic systems of the compounds of the invention preferably contain 6 to 14, most preferably 6, ring carbon atoms. Compounds which contain exclusively aromatic ring systems containing 6 ring carbon atoms—especially if the aromatic ring systems are not conjugated—particularly suitable whenever a low absorption in the UV and visible range is desired, hence typically for use as dissolution inhibitors in photoresists for the UV field.

Useful types of compounds of this invention include the compounds of formula II

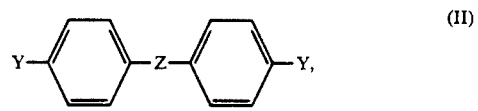

(II)

wherein Y is a tetrahydropyranyloxy substituent of formula I and Z is either a direct single bond or may be a member selected from the group consisting of: —S—; —O—; —SO—; —SO$_2$—; —CO—; —C(R$_6$)(R$_7$)—, where R$_6$ is hydrogen, methyl or aryl and R$_7$ is hydrogen or methyl. Particularly preferred divalent radicals —C(R$_6$)(R$_7$)— are —CH$_2$—; —C(CH$_3$)$_2$— and —C(CH$_3$)(Ph)—.

Also particularly preferred are the compounds of formula III

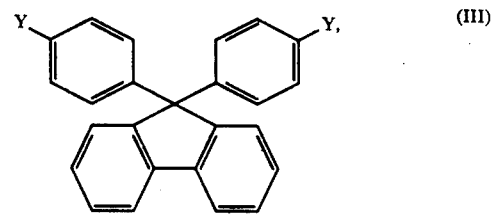

(III)

wherein Y is one of the tetrahydropyranyloxy substituents defined herein and which are derived from 9,9-bis(4-hydroxy)phenylfluorene.

Compounds of formula II or III are particularly preferred when they contain tetrahydropyranyloxy substituents of formula I, wherein $R_1$ is hydrogen, methyl or phenyl, $R_2$, $R_4$, $R_5$ are each hydrogen and $R_3$ is a saturated or an unsaturated acrylic hydrocarbon radical of 1 to 8 carbon atoms, or phenyl, preferably the compounds of formula

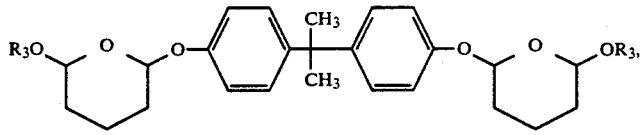

wherein $R_3$ is methyl, ethyl, isobutyl or phenyl, and the compounds of formula

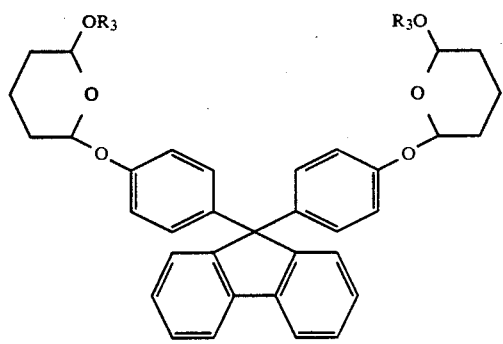

wherein $R_3$ is isobutyl or phenyl.

It will readily be understood that the aromatic ring systems of the compounds of this invention can contain other customary different substituents in addition to the above described tetrahydropyranyloxy substituents, especially $C_1$-$C_5$alkyl, $C_1$-$C_5$alkoxy, halogen and the like. Unsuitable, however, are those substituents which are able to increase substantially the solubility of the compounds of the invention in aqueous or aqueous-alkaline solutions, for example —COOH or readily soluble —COOMe groups (Me=metal).

The compounds of the invention can be prepared in a manner known per se, for example by an addition reaction of approximately stoichiometric amounts of an aromatic hydroxyl compound and suitable 3,4-dihydro-2H-pyrans, normally under anhydrous conditions and using a strong acid catalyst such as hydrochloric acid, boron trifluoride or p-toluenesulfonic acid. This method of preparation is described, for example, in the Journal of the American Chemical Society, 70, 4187–4189 (1948).

Particularly suitable hydroxyl compounds are aromatic polyhydroxy compounds which carry no hydroxyl groups at adjacent carbon atoms, typically 1,3-dihydroxybenzene, 1,4-dihydroxybenzene, 1,3,5-trihydroxybenzene, 2,2'-dihydroxybiphenyl, 2,2',4,4'-tetrahydroxybiphenyl, 4,4'-isopropylidenediphenol, 4,4'-oxydiphenol, 4,4'-sulfonyldiphenol, 2,4-oxydiphenol, 2,2'-sulfonyldiphenol, 1,1-bis(4-hydroxyphenyl)-1-phenylmethane, 1,1,1-tris(4-hydroxyphenyl)methane, 1-(3,5-dihydroxyphenyl)-1,1-diphenylmethane, 1,1-bis(3,5-dihydroxyphenyl)-1-phenylmethane, 1,1-bis(4-hydroxyphenyl)-1-phenylethane, 1,1,1-tris(4-hydroxyphenyl)ethane or 1,3,5-tris(4-hydroxyphenyl)benzene.

Suitable 2-alkoxy-3,4-dihydro-2H-pyrans and corresponding 2-alkenyloxy- or alkynyloxydihydropyrans and 2-aryloxy-3,4-dihydro-2H-pyrans as well as 2-alkoxyalkyl-3,4-dihydro-2H-pyrans and the corresponding 2-alkenyloxyalkyl- and 2-alkynyloxyalkyl derivatives as well as the 2-aryloxyalkyl-3,4-dihydro-2H-pyrans can be obtained by the cycloaddition of acrolein and the appropriate vinyl ether at elevated temperature in an autoclave, as described in U.S. Pat. No. 2,514,168. Further examples will be found, inter alia, in Beilstein, Supplement III, IV, Vol. 17, p. 1182–1195. Some 3,4-dihydropyrans suitable for the preparation of the compounds of the invention are commercially available.

The compounds of this invention can be used as dissolution inhibitors in photoresist systems. Acordingly, the invention also relates to a composition comprising a compound as described hereinabove, a compound which generates acid when exposed to actinic radiation, and a binder. Depending on the nature of the substituents at the tetrahydropyranyloxy groups of the inventive compounds, the polarity of the compounds and thus their inhibiting properties can be controlled within wide limits and substantially adapted to the remaining components of the resist system, especially the binder. For example, by using compounds containing relatively non-polar substituents as dissolution inhibitors it is possible to achieve a sufficient dissolution inhibition of non-irradiated zones of the resist film even in the presence of a binder such as poly(4-hydroxystyrene), which is highly soluble in aqueous-alkaline developers.

The compositions will normally contain 5–50% by weight of the aryltetrahydropryanyl ether compound, based on the total weight of non-volatile constituents in the composition. It is preferred to use 10–40% by weight of the compound.

A host of compounds are known as photosensitive components which generate an acid on exposure to light. Such compounds include the diazonium salts used in diazotype, the o-quinonedidazides used in known positive-working copying compositions, or also halogen compounds which form hydrohalic acid on exposure to radiation. Compounds of this type are disclosed, inter alia, in U.S. Pat. Nos. 3,515,552; 3,536,489 or 3,779,778, as well as in DE-A-2 718 259, 2 243 621 or 2 610 842.

Suitable photosensitive components of the composition of this invention are also cationic photoinitiators selected from the group of the iodonium or sulfonium salts. Such compounds are described in "UV-Curing, Science and Technology" (Editor: S. P. Pappas, Technology Marketing Corp., 642 Westover Road, Stanford, Conn. U.S.A.).

Diaryliodosyl salts are also particularly useful. Such compounds are disclosed, inter alia, in EP-A-106 797.

Sulfoxonium salts can also be used as photosensitive compounds. Such salts are disclosed, inter alia, in EP-B-35 969 or in EP-A-44 274 and 54 509. The aliphatic sulfoxonium salts which absorb in the deep-UV range and are disclosed in EP-A-164 314 merit special mention.

In particular it is also possible to use compounds which generate sulfonic acids on exposure to actinic light. Such compounds are known per se and are disclosed, inter alia, in GB-A 2 210 263, EP-A 84 515, 37 152 or 58 638 and in U.S. Pat. No. 4,258,121 or U.S. Pat. No. 4,371,605.

Salts used as photosensitive components which generate an acid are preferably soluble in organic solvents. Most preferably, these salts are precipitates with complex acids, typically hydroborofluoric acid or hexafluorophosphoric acid.

The amount of photosensitive component of the composition of this invention can vary within wide limits, depending on the nature and composition of the photosensitive composition. Useful results are obtained with c. 0.1 to 20% by weight of photosensitive component, based on the total content of volatile constituents in the composition. It is preferred to use 0.2 to 10% by weight of acid donor.

A binder must also be added to the photoresist compositions of the invention. The amount of binder can be from 30–90% by weight, preferably from 60–90% by weight, based on the total amount of binder, photosensitive component which generates acid, and inventive compound in the composition. It is preferred to use as binder a substance which is very readily soluble in alkali.

Very suitable binders are those based on phenolic compounds, for example novolaks which are derived from an aldehyde, preferably acetaldehyde or furfuraldehyde, but most preferably from formaldehyde and a phenol. The phenolic component of this binder is preferably phenol itself or also halogenated phenol, for example substituted by one or two chlorine atoms, preferably p-chlorophenol, or it is a phenol substituted by one or two $C_1$–$C_9$alkyl groups, typically o-, m- or p-cresol, a xylenol, p-tert-butylphenol or p-nonylphenol. The phenol component of the preferred novolaks may also, however, be p-phenylphenol, resorcinol, bis(4-hydroxyphenyl)methane or 2,2-bis(4-hydroxyphenyl)-propane.

Some of the phenolic hydroxy groups of these novolaks may also be modified by reaction with chloroacetic acid, isocyanates, epoxides, carboxylic anhydrides, carbonyl chlorides or sulfonyl chlorides.

Poly(4-hydroxystyrenes) are also very suitable binders.

The compositions of this invention may contain further conventional modifiers such as stabilisers, pigments, dyes, fillers, adhesion promoters, flow control agents, wetting agents and plasticisers. For application, the compositions may also be dissolved in a suitable solvent.

The compositions of this invention have excellent suitability as coating compositions for all kinds of substrates, such as wood, textiles, paper, ceramics, glass, plastics materials such as polyester, polyethylene terephthalate, polyolefins or cellulose acetate, preferably in the form of films and of metals, typically Al, Cu, Ni, Fe, Zn, Mg or Co, and of Si or $SiO_2$, on which it is desired to apply an image by imagewise exposure.

Depending on their handling, the compositions can be used as positive-working and as negative-working photoresist systems. The resist system is positive-working if development is carried out after exposure of a suitable layer to radiation direct or after only gentle heating. The compounds of the invention in this case act as dissolution inhibitors for the layer at the unexposed areas. Whereas the compounds are relatively poorly soluble in the aqueous alkaline solutions customarily used as developers for positive resist systems, they are readily soluble after the acid-catalysed of cleavage of the ether linkage induced by the irradiation. However, if the resist systems are heated after irradiation to temperature above 100° C., then a reversal of tonality can be achieved and they become negative-working. They can, however, also be developed, without swelling, with the aqueous alkaline developers of higher concentration mentioned above which, however, then dissolve the unexposed areas of the layer better then the exposed areas.

The invention therefore also relates to a process for producing positive images comprising the following steps:

coating a substrate with a photosensitive composition as defined above, and exposing the coated substrate to actinic radiation in a predetermined pattern, and, after optional brief heating to a temperature below 100° C., dissolving out the exposed areas of the layer with a developer.

To carry out the process it is usual to prepare first a solution of the composition. The choice of solvent and the concentration depends mainly on the nature of the composition and on the coating method. The solution is uniformly applied to a substrate by known coating methods, for example by spin-coating, immersion, doctor coating, curtain coating, brushing, spraying and reverse roller coating. It is also possible to apply the light-sensitive layer to a temporary flexible support and then to coat the final substrate, for example a copper-clad circuit board, by coat transfer by means of lamination.

The add-on (layer thickness) and the nature of the substrate are contingent on the desired utility. This thickness range comprises values of c. 0.5 $\mu$m to more than 100 $\mu$m.

Possible utilities of the compositions of this invention are as photoresists in the electronics field, the production of printing plates such as offset plates or screen printing formes, mould etching, and, in particular as microresist in the production of integrated circuits. The possible substrates and conditions for processing the coated substrates differ correspondingly.

When using the compositions as microresists for integrated and large-scale integrated circuits, the layer thickness are typically from 0.5 to 10 $\mu$m, preferably from 0.5 to 5 $\mu$m, most preferably from 0.5 to 1.5 $\mu$m.

After the substrate has been coated, the solvent is normally removed by drying to give a layer of photoresist on the substrate. The coatings have a particularly fine and smooth surface without cracks.

After conventional imagewise exposure of the material, the coated substrate can be developed direct in a developer or subjected to a brief heat treatment for about 5 minutes (post-exposure bake), which can lead to an increase in the solubility rate of the irradiated resist material. The temperature must remain below 100° C. and should preferably not exceed 60° C.

The exposed areas of the photoresist are washed out with a developer. The choice of the developer depends on the type of photoresist, especially on the nature of the binder used or of the photolysis products. The developer may comprise aqueous solutions of bases to which organic solvents or mixtures thereof may be added. It is preferred to use an aqueous solution of a base as developer.

Suitable developers for producing positive structures are typically the aqueous-alkaline solutions used for the development of naphthoquinone diazide/novolak resists. These include in particular aqueous solutions of alkali metal silicates, phosphates and hydroxides.

A particular advantage of the positive photoresists of this invention is that they exert excellent inhibition in metal ion-free developers (MIF developers). These are typically aqueous solutions of tetraalkylammonium hydroxides, such as $N(CH_3)_4OH$ or $N(C_4H_9)_4OH$, which are often desired for the production of integrated circuits to avoid contamination by metals.

The aqueous developer solutions may additionally contain minor amounts of wetting agents and/or organic solvents.

Typical organic solvents are those which are miscible with water and can be added to the developer liquids, for example 2-ethoxyethanol or acetone, as well as mixtures of two or more such solvents. A typical aqueous-organic developer system is Butylcellosolve ®/water.

The expression "exposure to actinic radiation in a predetermined pattern" will be understood to mean exposure through a photomask which contains a predetermined pattern, for example a photographic transparency, as well as exposure to a laser beam which is moved by logic control over the surface of the coated surface to produce an image.

The light-sensitivity of the compositions of this invention extends generally from the UV region (ca. 200 nm) to ca. 600 nm and is thus very wide ranging. Suitable light sources therefore comprise a large number of very widely varying types. Point light sources as well as arrays of reflector lamps are suitable. Examples are: carbon arc, xenon arcs, mercury vapour lamps which may be doped with halogen atoms (metal halide lamps), fluorescent lamps, argon glow lamps, electronic flash lamps and photographic flood lamps. The distance between lamp and image material may vary substantially, depending on the utility and the type of lamp, for example, from 2 cm to 150 cm. Particularly suitable light sources are laser light sources, for example argon ion lasers or crypton ion lasers. With this type of exposure, a photomask in contact with the photopolymer layer is no longer necessary, as the laser beam writes direct on to the layer. The high sensitivity of the compositions of the invention is very advantageous here and permits high writing speeds at relatively low intensities.

The light-sensitive compositions may also contain sensitisers to enhance the spectral sensitivity in a specific wavelength range. Thse sensitisers include Michlers ketone, benzophenones, thioxanthones or aromatic hydrocarbons such as anthracene, substituted anthracenes, pyrene or perylene.

Positive-working photoresist layers of this invention can be used with particular advantage in the UV range, especially in the deep-UV range, in which range exposure is carried out with the radiation of a wavelength below c. 300 nm which is filtered out from the light of mercury vapour lamps or produced by excimer lasers.

Particularly suitable photoresist compositions are those in which the binder is poly(4-hydroxystyrene). Poly(4-hydroxystyrene) is a resin which, compared with novolaks, absorbs only extremely weakly in the deep-UV range. After imagewise exposure and development, the compositions of the invention therefore result in resist structures whose profiles, as defines, are almost vertical. If, on the other hand, the binder of a photoresist layer absorbs in the wavelength range which is used for exposure, then the consequence is that the irradiated light is absorbed particularly strongly in the upper layers of the resist film and only a relatively minor amount penetrates into the deeper resist layer and is able to become active there. The consequence is in turn that the profiles of the resist structures are nowhere near vertical, but become increasingly thick with increasing depth. Poly(4-hydroxystyrene) has the property that, in comparison with novolaks, it is very readily soluble in the aqueous alkaline developers normally used in practice. Hitherto its use as binder in photoresists for this type of developer has hardly been possible, as there were no dissolution inhibitors available which could effect a sufficiently large difference in solubility between the exposed and unexposed parts of the layer. The use of the compounds of this invention as dissolution inhibitors now makes it possible to to compensate very easily for the better solubility of poly(4-hydroxystyrene) as compared with novolaks by using inventive compounds which carry those tetrahydropyranyloxy substituents which have relatively non-polar radicals, especially non-polar radicals $R_3$, such as isobutyl or phenyl.

As the dissolution inhibitors of this invention are based on the principle of chemical amplification, these photoresists are very sensitive. This high sensitivity is especially useful because many sources of radiation have only a very weak intensity below 300 nm. The inventive photoresist compositions are preferably irradiated with doses in the range from 50 $mJ/cm^2$ to 5 $mJ/cm^2$, while favorable exposure times are possible. Even lower irradiation doses than these are possible in some cases.

When irradiating with light from the deep-UV range, it is entirely possible with the inventive photoresists to image structures in the submicron range, typically from 0.5 to 1 $\mu m$. This method is therefore particularly suitable for the production of large-scale integrated circuits. The undissolved areas remaining after subsequent development have almost vertical side walls.

The contrast of the resists is in general good, especially when the dissolution inhibitor used is a compound of formula I containing a hydrocarbon radical $R_3$ which is also relatively easily removable by acid catalysis, for example a hydrocarbon having allylic unsaturation. The resists also exhibit a very insignificant rate of loss at the unexposed areas when being developed.

A further advantage of the inventive photoresist compositions is that they do not absolutely need to be exposed to the aforementioned post-exposure bake when producing positive images between exposure and development in order to make the exposed areas sufficiently soluble. It is thereby possible to avoid a process step which is necessary in the prior art when using positive photoresist systems which are based on the principle of chemical amplification.

The invention further relates to a process for the production of negative images comprising the following steps:

coating a substrate with a composition as described hereinabove, exposing the coated substrate in a predetermined pattern to actinic light and subsequent heating to a temperature in the range from 100° to 170° C., as well as dissolving out the unexposed areas of the layer with a developer.

Coating and exposure can be effected in the same manner as explained above in connection with the process for the production of positive images. However, between exposure and exposure the resist layer must then be heated for preferably about 5 to 120 seconds to a temperature in the range from 100° to 170° C. The exposed areas of the resist are chemically changed by this heat treatment such that the resist material at these areas is virtually insoluble in the conventional aqueous-alkaline developer solutions for positive photoresists, even if developer solutions of very high concentration are used. Even concentrations which result in the resolution of unexposed resist material no longer attack said material at the exposed areas, so that the unexposed resist can be dissolved out, i.e. a negative image is formed.

As already mentioned, the developers suitable for positive resists must be used in in the process of this invention for the production of negative images in higher concentrations than would be suitable for corresponding positive-working photoresist layers in which the unexposed areas may not, of course, be resolved. The person skilled in the art can easily determine suitable concentrations by making one or two experiments. Commercially obtainable developers for positive photoresists are often suitable if they are used undiluted. Normally no swelling of the resist layer occurs during development.

The invention further relates to the products obtainable by means of the described process, especially those which have artificially produced structural features of less than 1 μm.

EXAMPLE 1

Preparation of the bis[2-(6-ethoxy)tetrahydropyranyl]ether of 4,4'-isopropylidenediphenol (A)

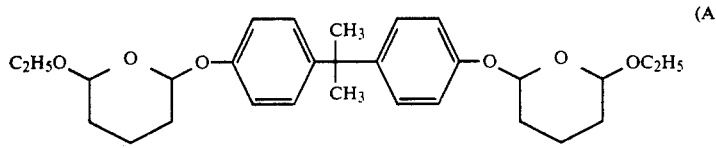
(A)

In a 150 ml 3-necked round flask equipped with magnetic stirrer, internal thermometer, dropping funnel and nitrogen inlet, 10.0 g (78 mmol) of 2-ethoxy-3,4-dihydro-2H-pyran (ex Aldrich) are slowly added dropwise at 5° C. to a mixture of 8.9 g (39 mmol) of 4,4'-isopropylidenediphenol (bisphenol A) and 0.18 g of p-toluenesulfonic acid in 100 ml of ether. The cooling is removed after 30 minutes. Then the reaction is allowed to go to completion for 15 h at 20° C. The reaction mixture is neutralised with 0.5N NaOH solution, and the combined ether extracts are washed three times with water. The ether phase is dried over magnesium sulfate and concentrated, giving 18.7 g (98%) of pure product (NMR spectroscopy) as a clear, viscous oil.

NMR spectrum: (100 MHz, CDCl$_3$): 7.15 (d, 4H); 6.99 (d, 4H); 5,63 (m, 2H); 4.91 (m, 2H); 4.0–3.3 (m, 4H); 2.1–1.85 (m, 12H); 1.63 (s, 6H); 1.15 (t, 6H).

EXAMPLE 2

A resist solution is prepared by dissolving 25 parts of the bis[2-(6-ethoxy)tetrahydropyranyl]ether of 4,4'-isopropylidenediphenol of Example 1, 75 parts of a poly(p-hydroxystyrene) (Resin M ®, ex Maruzen Oil) and 5 parts of triphenylsulfonium hexafluoroarsenate in 250 parts of cyclohexanone.

The resist solution is spin-coated onto 4 inch silicon wafers at 2500 rpm and dried at 120° C. for 2 minutes to give homogeneous films having a layer thickness of 0.75 μm.

The films are contact exposed through a chromium quartz mask with superfine structures of 0.5 μm with light of 254 nm wavelength (interference filter, 10 nm band width). The light source is a mercury vapour lamp; the irradiation dose is 3 mJ/cm$^2$.

Immediately afterwards development is carried out with a 0.2N NaOH solution, giving 0.5 μm l/s (=lines and spaces ≙ adjacent exposed and unexposed areas of equal width) of good resolution and with almost wall profiles.

EXAMPLE 3

Preparation of the bis[2-(6-isobutoxy)tetrahydropyranyl]ether of 9,9'-bis(4-hydroxyphenyl)fluorene

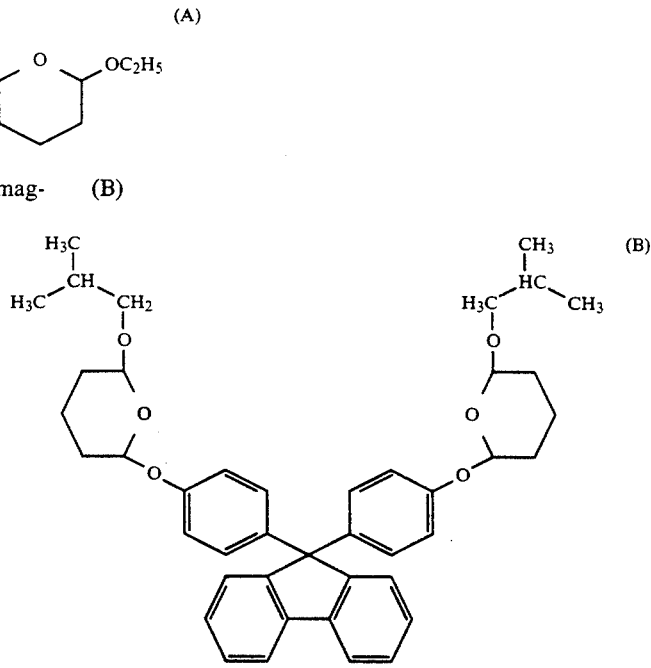
(B)

In a 250 ml 3-necked round flask equipped with magnetic stirrer, internal thermometer, dropping funnel and nitrogen inlet, 8.6 g (55 mmol) of 2-isobutoxy-3,4-dihydro-2H-pyran are slowly added dropwise at 20° C. to 8.8 g (25 mmol) of 9,9-bis(4-hydroxyphenyl)fluorene and 0.1 g of p-toluenesulfonic acid in 200 ml of diethyl ether. The reaction is allowed to go to completion for 20 h and then 100 ml of 1N NaOH solution are added.

The organic phase is washed twice with water, dried over magnesium sulfate and concentrated, giving 14 g (21 mmol, 84%) of the desired product as a colourless powder which can be further purified by recrystallisation from n-hexane.

Melting point (uncorrected): 83° C.

$^1$H-NMR (100 MHz): 7.6–6.6 (m, 16H); 5.6 (m, 2H); 4.8 (m, 2H); 3.4 (dd, 2H); 3.0 (dd, 2H); 1.9–1.5 (m, 14H); 0.8 (d, 12H)

TGA (10°/min): −5% at 233° C.; −37% at 290° C.

EXAMPLE 4

A resist solution is prepared by dissolving 25 parts of the bis[2-(6-isobutoxy)tetrahydropyranyl]ether of 9,9′-bis(4-hydroxyphenyl)fluorene of Example 3, 75 parts of poly(p-hydroxystyrene) (Resin M ®) and 5 parts of triphenylsulfonium (trifluoromethanesulfonate), referred to hereinafter also as triphenylsulfonium triflate, in 250 parts of cyclohexanone.

The resist solution is spin-coated onto 4 inch silicon wafers at 4000 rpm and dried at 120° C. for 2 minutes to give homogeneous films having a layer thickness of 1.0 μm.

The films are then contact exposed through a chromium quartz mask with superfine structures of 0.5 μm with a dose of 20 mJ/cm². Immediately afterwards development is carried out with a 0.17N NaOH solution. Positive structure sin the submicron range are imaged.

EXAMPLE 5

Coated 4 inch silicon wafers of Example 4 are exposed through a chromium quartz mask with a dose of 5 mJ/cm². The material is thereafter heated for 30 seconds to 130° C. and then developed in a 2.38% solution of tetramethylammonium hydroxide, the unexposed areas being dissolved out. The material exhibits no swelling during the development process and permits the production of negative images with superfine structures of 0.5 μm l/s.

EXAMPLE 6

Preparation of the bis[2-(6-ethoxy)tetrahydropyranyl]ether of 9,9′-bis(4-hydroxyphenyl)fluorene (C)

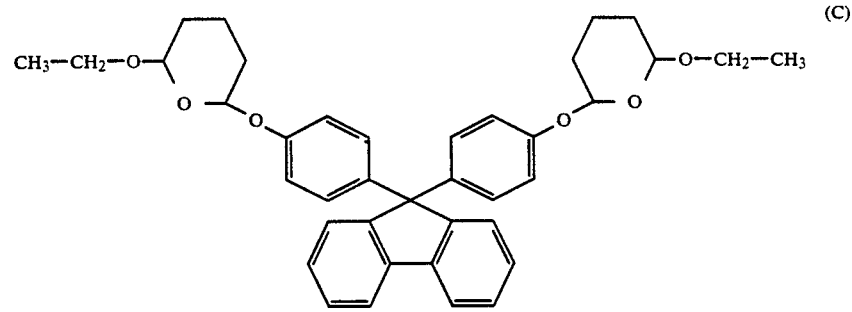

In a 250 ml 3-necked round flask equipped with magnetic stirrer, internal thermometer, dropping funnel and nitrogen inlet, 7.0 g (55 mmol) of 2-ethoxy-3,4-dihydro-2H-pyran are slowly added dropwise at 20° C. over 20 h to 8.8 g (25 mmol) of 9,9-bis(4-hydroxyphenyl)fluorene and 0.1 g of p-toluenesulfonic acid in 200 ml of diethyl ether. The reaction is allowed to go to completion for 20 h at 20° C. and then 100 ml of 1N NaOH solution are added. The organic phase is washed twice with water, dried over magnesium sulfate and concentrated, giving 10 g (17 mmol, 68%) of the desired product as a white substance which can be further purified by recrystallisation from n-hexane.

Melting point (uncorrected): 110° C.

$^1$H-NMR (100 MHz): 7.8–6.6 (m, 16H); 5.6 (m, 2H); 4.8 (m, 2H); 3.7 (q, 2H); 3.4 (q, 2H); 2.0–1.6 (m, 12H); 1.1 (t, 6H)

TGA (10°/min): −5% at 237° C.; −33% at 300° C.

EXAMPLE 7

A resist solution is prepared as in Example 4 by dissolving 25 parts of tetrahydropyranyl ether of Example 6, 75 parts of Resin-M ® and 5 parts of triphenylsulfonium triflate in 250 parts of cyclohexanone and spin-coated onto a silicon wafer. After drying at 120° C. for 2 minutes, homogeneous resist films having a layer thickness of 0.9 μm are obtained. Imagewise exposure with a dose of 20 mJ/cm² at 254 nm and subsequent development as in Example 2 gives accurate positive image structures.

EXAMPLE 8

Preparation of the bis[2-(6-methoxy)tetrahydropyranyl]ether of 1,1-bis(4-hydroxyphenyl-1-phenylethane) (D)

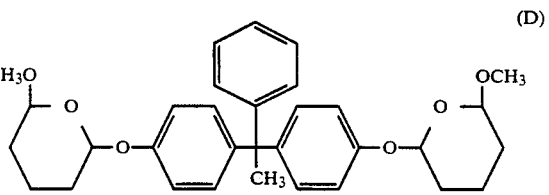

In a 100 ml 3-necked round flask equipped with magnetic stirrer, internal thermometer, dropping funnel and nitrogen inlet, 6.5 g (57 mmol) of 2-methoxy-3,4-dihydro-2H-pyran are slowly added dropwise at 20° C. to 7.5 g (26 mmol) of bisphenol C (1,1-bis(4-hydroxyphenyl)phenylethane) and 0.15 g of p-toluenesulfonic acid in 40 ml of diethyl ether. The reaction is allowed to continue for 20 h at 20° C. and then 100 ml of 1N NaOH solution are added. The organic phase is washed twice with water, dried over magnesium sulfate and concentrated, giving 7.3 g (14 mmol, 54%) of the desired product as a white powder which can be further purified by recrystallisation from n-hexane.

Melting point (uncorrected): 60° C.

$^1$H-NMR (100 MHz): 7.4–6.7 (m, 13H); 5.6 (m, 2H); 4.8 (m, 2H); 3.7 (s, H); 2.2–1.6 (m, 12H)

Elemental analysis: C: cal. 74.11%; found 74.97%; H: cal. 7.39%; found 7.13%

EXAMPLE 9

A resist solution is prepared as in Example 4 by dissolving 25 parts of the bis[2-(6-methoxy)tetrahydropyranyl]ether of 1,1-bis(4-hydroxypheny)-1-phenylethane (D) of Example 8, 75 parts of Resin-M ® and 5 parts of triphenylsulfonium triflate in 250 parts of cyclopentanone and spin-coated onto a silicon wafer. After drying at 20° C. for 2 minutes, resist films having a layer thickness of 1.2 μm are obtained with an optical density (quartz disc) of 0.51. Imagewise exposure as in Example 2 or Example 4 and subsequent development with 0.17 N NaOH gives positive image structures in the submicron range.

EXAMPLE 10

45 g (375 mmol) of phenylvinyl ether, 21 g (375 mmol) of acrolein and 0.66 g (6 mmol) of hydroquinone are reacted in a pressure reactor for 1 h at 185° C. After cooling, 2-phenoxy-3,4-dihydro-2H-pyran is isolated by distillation at 80° C./0.0267 kPa in a yield of 30.2 (172 mmol; 46%) as a clear liquid.

Boiling point: 80° C./0.0267 kPa $^1$H-NMR (100 MHz): 7.26 (m, 2H); 7.1–6.9 (m, 3H); 6.22 (d, 1H); 5.68 (m, 1H); 4.83 (m, 1H); 2.4–2.2 (m, 1H); 1.85–2.2 (m, 3H)

EXAMPLE 11

Preparation of the bis[2-(6-phenoxy)tetrahydropyranyl]ether of 4,4'-isopropylidenediphenol (E)

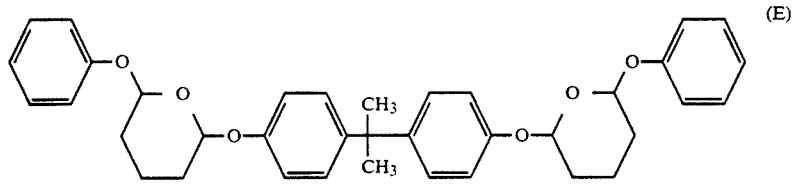

In a 100 ml 3-necked round flask equipped with magnetic stirrer, internal thermometer, dropping funnel and nitrogen inlet, 3.9 g (22 mmol) of 2-phenoxy-3,4-dihydro-2H-pyran are slowly added dropwise at 10° C. to 2.3 g (10 mmol) of 4,4'-isopopylidenediphenol (bisphenol A) and 50 mg of p-toluenesulfonic acid in 30 ml of diethyl ether. The reaction mixture is brought to room temperature and the reaction is allowed to go to completion for 30 h. Finally, 50 ml of 1N NaOH solution are added. The organic phase is washed twice with water, dried over magnesium sulfate and concentrated, giving 4.7 g (8.1 mmol, 81%) of the desired product as a colourless viscous oil. The product can be further purified by recrystallisation from methanol.

Melting point (uncorrected): 54° C.

$^1$H-NMR (100 MHz): 7.3–6.7 (m, 18H); 5.7 (m, 4H); 2.2–1.7 (m, 12H); 1.6 (m, 6H) TGA (10°/min): −5% at 225° C.; −47% at 293° C.

EXAMPLE 12

A resist solution is prepared by dissolving 25 parts of the bis[2-(6-phenoxy)tetrahydropyranyl]ether of 4,4'-isopropylidenediphenol of Example 10, 75 parts of Resin-M ® and 5 parts of triphenylsulfonium triflate in 250 parts of cyclopentanone and spin-coated onto a 4 inch silicon wafer or 1 inch quartz disc at 3500 rpm. After drying at the material at 120° C. for 2 minutes, resist films having a layer thickness of 1.1 μm are obtained with an optical density of 0.48 at 254 nm.

The coated silicon wafer is then imagewise exposed through a quartz mask whose smallest structures are 0.5 μm. The light source is a mercury vapour pressure lamp having a 254 nm interference filter with a band width of 10 nm in its path of rays. The irradiation dose is 20 mJ/cm$^2$. Immediately after exposure, development is made with a developer based on tetramethylammonium hydroxide and an accurate positive image of the mask structures is obtained.

What is claimed is:

1. A composition comprising (1) a non-polymeric compound which contains at least one aromatic ring system carrying one or more tetrahydropyranyloxy substituents of formula I

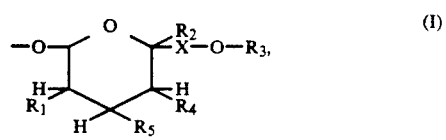

wherein $R_1$ is hydrogen, halogen, alkyl, cycloalkyl, aryl, alkoxy or aryloxy, $R_2$ is hydrogen, alkyl, cycloalkyl or aryl, $R_3$ is a saturated or unsaturated hydrocarbon radical, $R_4$ and $R_5$ are each independently of the other hydrogen, halogen, alkyl, alkoxy or aryloxy, and X is a direct single bond or a methylene or ethylene bridge, (2) a compound which generates acid when exposed to actinic radiation, and (3) a binder.

2. A composition according to claim 1, wherein in the compound of formula (I), $R_1$ is hydrogen, halogen, $C_1$–$C_5$alkyl, phenyl, substituted phenyl, $C_1$–$C_5$alkoxy, phenoxy or substituted phenoxy, $R_2$ is hydrogen, $C_1$–$C_5$alkyl or phenyl, $R_3$ is a saturated or unsaturated hydrocarbon radical of 1 to 20 carbon atoms, and $R_4$ and $R_5$ are each independently of the other hydrogen, halogen, $C_1$–$C_5$alkyl, $C_1$–$C_5$alkoxy, phenoxy or substituted phenoxy.

3. A composition according to claim 2, wherein in the compound of formula (I), $R_1$ is hydrogen, methyl or phenyl, $R_2$, $R_4$, $R_5$ are each hydrogen, and $R_3$ is a saturated or unsaturated acyclic hydrocarbon radical of 1 to 8 carbon atoms or is phenyl.

4. A composition according to claim 1, wherein in the compound of formula (I), X is a direct bond.

5. A composition according to claim 1, wherein the compound of formula (I) contains a maximum of 100 atoms in the molecule, including all carbon and hetero atoms but not the hydrogen atoms and any atom of the tetrahydropyranyloxy groups, at least 75% of which atoms belong to aromatic systems, said compound containing at least two tetrahydropyranyloxy substituents of formula I and the total number of substituents of formula I present therein being at least so great that there is at least one substituent of formula I for every two aromatic rings in the compound, the expression "aromatic rings" being understood as meaning the individual aromatic rings of an aromatic system.

6. A composition according to claim 1, in which the compound of formula (I) contains as aromatic systems solely non-conjugated systems containing 6 ring carbon atoms.

7. A composition according to claim 6 in which the compound of formula (I) contains as aromatic systems solely non-conjugated systems containing 6 ring carbon atoms of formula II or III

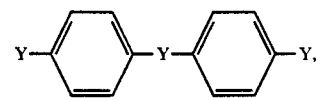

(II)

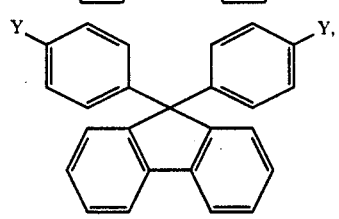

(III)

wherein Y is a tetrahydropyranyloxy substituent of formula I and Z is either a direct single bond or a member selected from the group consisting of: —S—; —O—; —SO—; —SO$_2$—; —CO—; and —C(R$_6$)(R$_7$)—, where R$_6$ is hydrogen, methyl or aryl and R$_7$ is hydrogen or methyl.

* * * * *